United States Patent
Dussault et al.

(10) Patent No.: US 8,189,738 B2
(45) Date of Patent: May 29, 2012

(54) METHODS AND SYSTEMS FOR GUIDING CLINICAL RADIOTHERAPY SETUPS

(75) Inventors: Chantal Dussault, Verdun (CA); Martin Lachaine, Montreal (CA); Daniel Lodu, Stittsville (CA); Martin Bonneville, Montreal (CA)

(73) Assignee: Elekta Ltd., Quebec (CA)

( * ) Notice: Subject to any disclaimer, the term of this patent is extended or adjusted under 35 U.S.C. 154(b) by 164 days.

(21) Appl. No.: 12/473,506

(22) Filed: May 28, 2009

(65) Prior Publication Data

US 2010/0008467 A1 Jan. 14, 2010

Related U.S. Application Data

(60) Provisional application No. 61/058,049, filed on Jun. 2, 2008.

(51) Int. Cl.
*A61N 5/10* (2006.01)
(52) U.S. Cl. .......................................................... 378/65
(58) Field of Classification Search .................. 378/62, 378/64, 65, 68, 145, 147
See application file for complete search history.

(56) References Cited

U.S. PATENT DOCUMENTS

| | | | |
|---|---|---|---|
| 3,082,322 A | 3/1963 | Koerner at al. |
| 3,777,124 A | 12/1973 | Pavkovich |
| 3,987,281 A | 10/1976 | Hodes |
| 3,991,310 A | 11/1976 | Morrison |
| 4,118,631 A | 10/1978 | Froggatt |
| 4,618,978 A | 10/1986 | Cosman |
| 4,882,741 A | 11/1989 | Brown |
| 4,923,459 A | 5/1990 | Nambu |
| 4,943,990 A | 7/1990 | Schar |
| 5,039,867 A | 8/1991 | Nishihara et al. |
| 5,080,100 A | 1/1992 | Trotel |
| 5,086,401 A | 2/1992 | Glassman et al. |
| 5,099,846 A | 3/1992 | Hardy |
| 5,107,839 A | 4/1992 | Houdek et al. |
| 5,117,829 A | 6/1992 | Miller et al. |
| 5,138,647 A | 8/1992 | Nguyen et al. |
| 5,207,223 A | 5/1993 | Adler |
| 5,222,499 A | 6/1993 | Allen et al. |
| 5,233,990 A | 8/1993 | Barnea |
| 5,291,889 A | 3/1994 | Kenet et al. |
| 5,295,483 A | 3/1994 | Nowacki et al. |
| 5,299,288 A | 3/1994 | Glassman et al. |
| 5,301,674 A | 4/1994 | Erikson et al. |

(Continued)

FOREIGN PATENT DOCUMENTS

CA 2416887 A1 2/2002

(Continued)

OTHER PUBLICATIONS

International Search Report and Written Opinion for PCT/CA2009/000750, mailed Sep. 18, 2009 (8 pages).

(Continued)

*Primary Examiner* — Irakli Kiknadze
(74) *Attorney, Agent, or Firm* — Goodwin Procter LLP

(57) ABSTRACT

Radiation beam parameters are determined by manipulating a tool about a patient in order to determine a desired beam entry point and/or beam angle. In certain embodiments, a visual representation of the beam may be displayed along with images of internal and external anatomical features of the patient, and used to determine couch and/or gantry manipulation parameters to move the patient into a desired position with respect to a treatment delivery device.

28 Claims, 6 Drawing Sheets

U.S. PATENT DOCUMENTS

| | | |
|---|---|---|
| 5,379,642 A | 1/1995 | Reckwerdt et al. |
| 5,389,101 A | 2/1995 | Heilbrun et al. |
| 5,391,139 A | 2/1995 | Edmundson |
| 5,397,329 A | 3/1995 | Allen |
| 5,408,101 A | 4/1995 | Wong |
| 5,411,026 A | 5/1995 | Carol |
| 5,438,991 A | 8/1995 | Yu et al. |
| 5,442,675 A | 8/1995 | Swerdloff et al. |
| 5,446,548 A | 8/1995 | Gerig et al. |
| 5,447,154 A | 9/1995 | Cinquin et al. |
| 5,483,961 A | 1/1996 | Kelly et al. |
| 5,511,549 A | 4/1996 | Legg et al. |
| 5,524,627 A | 6/1996 | Passi |
| 5,531,227 A | 7/1996 | Schneider |
| 5,553,618 A | 9/1996 | Suzuki et al. |
| 5,591,983 A | 1/1997 | Yao |
| 5,603,318 A | 2/1997 | Heilbrun et al. |
| 5,609,485 A | 3/1997 | Bergman et al. |
| 5,645,066 A | 7/1997 | Gandini et al. |
| 5,673,300 A | 9/1997 | Reckwerdt et al. |
| 5,690,108 A | 11/1997 | Chakeres |
| 5,715,166 A | 2/1998 | Besl et al. |
| 5,734,384 A | 3/1998 | Yanof et al. |
| 5,740,225 A | 4/1998 | Nabatame |
| 5,754,623 A | 5/1998 | Seki |
| 5,757,881 A | 5/1998 | Hughes |
| 5,778,043 A | 7/1998 | Cosman |
| 5,810,007 A | 9/1998 | Holupka et al. |
| 5,836,954 A | 11/1998 | Heilbrun et al. |
| 5,851,183 A | 12/1998 | Bucholz |
| 5,859,891 A | 1/1999 | Hibbard |
| 5,952,577 A | 9/1999 | Passi |
| 5,991,703 A | 11/1999 | Kase |
| 6,019,724 A | 2/2000 | Gronningsaeter et al. |
| 6,038,283 A | 3/2000 | Carol et al. |
| 6,094,508 A | 7/2000 | Acharya et al. |
| 6,106,470 A | 8/2000 | Geiser et al. |
| 6,112,341 A | 9/2000 | Moreland |
| 6,117,081 A | 9/2000 | Jago et al. |
| 6,119,033 A | 9/2000 | Spigelman et al. |
| 6,122,341 A | 9/2000 | Butler et al. |
| 6,129,670 A | 10/2000 | Burdette et al. |
| 6,144,875 A | 11/2000 | Schweikard et al. |
| 6,146,390 A | 11/2000 | Heilbrun et al. |
| 6,198,957 B1 | 3/2001 | Green |
| 6,208,883 B1 | 3/2001 | Holupka et al. |
| 6,259,943 B1 | 7/2001 | Cosman et al. |
| 6,269,143 B1 | 7/2001 | Tachibana |
| 6,285,805 B1 | 9/2001 | Gueziec |
| 6,292,578 B1 | 9/2001 | Kalvin |
| 6,307,914 B1 | 10/2001 | Kunieda et al. |
| 6,314,310 B1 | 11/2001 | Ben-Haim et al. |
| 6,325,758 B1 | 12/2001 | Carol et al. |
| 6,345,114 B1 | 2/2002 | Mackie et al. |
| 6,359,959 B1 | 3/2002 | Butler et al. |
| 6,366,798 B2 | 4/2002 | Green |
| 6,385,286 B1 | 5/2002 | Fitchard et al. |
| 6,385,288 B1 | 5/2002 | Kanematsu |
| 6,390,982 B1 | 5/2002 | Bova et al. |
| 6,405,072 B1 | 6/2002 | Cosman |
| 6,423,009 B1 | 7/2002 | Downey et al. |
| 6,438,202 B1 | 8/2002 | Olivera et al. |
| 6,459,769 B1 | 10/2002 | Cosman |
| 6,491,702 B2 | 12/2002 | Heilbrun et al. |
| 6,511,430 B1 | 1/2003 | Sherar et al. |
| 6,516,046 B1 | 2/2003 | Frohlich et al. |
| 6,535,574 B1 | 3/2003 | Collins et al. |
| 6,546,073 B1 | 4/2003 | Lee |
| 6,553,152 B1 | 4/2003 | Miller et al. |
| 6,560,311 B1 | 5/2003 | Shepard et al. |
| 6,567,684 B1 | 5/2003 | Chenevert et al. |
| 6,591,127 B1 | 7/2003 | McKinnon |
| 6,600,810 B1 | 7/2003 | Hughes |
| 6,621,889 B1 | 9/2003 | Mostafavi |
| 6,628,983 B1 | 9/2003 | Gagnon |
| 6,631,284 B2 | 10/2003 | Nutt et al. |
| 6,636,622 B2 | 10/2003 | Mackie et al. |
| 6,641,539 B2 | 11/2003 | Hirooka et al. |
| 6,661,870 B2 | 12/2003 | Kapatoes et al. |
| 6,662,036 B2 | 12/2003 | Cosman |
| 6,669,635 B2 | 12/2003 | Kessman et al. |
| 6,683,985 B1 | 1/2004 | Kase et al. |
| 6,690,965 B1 | 2/2004 | Riaziat et al. |
| 6,714,627 B1 | 3/2004 | Brown et al. |
| 6,725,079 B2 | 4/2004 | Zuk et al. |
| 6,728,424 B1 | 4/2004 | Zhu et al. |
| 6,731,970 B2 | 5/2004 | Schlossbauer et al. |
| 6,750,873 B1 | 6/2004 | Bernardini et al. |
| 6,754,374 B1 | 6/2004 | Miller et al. |
| 6,785,409 B1 | 8/2004 | Suri |
| 6,804,548 B2 | 10/2004 | Takahashi et al. |
| 6,914,959 B2 | 7/2005 | Bailey et al. |
| 6,915,008 B2 | 7/2005 | Barman et al. |
| 6,968,224 B2 | 11/2005 | Kessman et al. |
| 6,980,679 B2 | 12/2005 | Jeung et al. |
| 7,092,109 B2 | 8/2006 | Satoh et al. |
| 7,095,823 B2 | 8/2006 | Topolnjak et al. |
| 7,260,426 B2 | 8/2007 | Schweikard et al. |
| 7,333,644 B2 | 2/2008 | Jerebko et al. |
| 7,343,030 B2 | 3/2008 | Sawyer |
| 7,430,321 B2 | 9/2008 | Okada et al. |
| 7,438,685 B2 | 10/2008 | Burdette et al. |
| 7,535,411 B2 | 5/2009 | Falco |
| 7,613,501 B2 * | 11/2009 | Scherch ..................... 600/427 |
| 7,634,304 B2 | 12/2009 | Falco et al. |
| 7,662,097 B2 | 2/2010 | Falco et al. |
| 7,672,705 B2 | 3/2010 | Lachaine et al. |
| 7,729,744 B2 | 6/2010 | Falco et al. |
| 7,801,349 B2 | 9/2010 | Wang et al. |
| 1,006,981 A1 | 3/2011 | Nord at al. |
| 2001/0035871 A1 | 11/2001 | Bieger et al. |
| 2001/0049475 A1 | 12/2001 | Bucholz et al. |
| 2002/0018588 A1 | 2/2002 | Kusch |
| 2002/0065461 A1 | 5/2002 | Cosman |
| 2002/0082494 A1 | 6/2002 | Balloni et al. |
| 2002/0087101 A1 | 7/2002 | Barrick et al. |
| 2002/0122530 A1 | 9/2002 | Erbel et al. |
| 2002/0156375 A1 | 10/2002 | Kessman et al. |
| 2002/0176541 A1 | 11/2002 | Schubert et al. |
| 2002/0183610 A1 | 12/2002 | Foley et al. |
| 2002/0188194 A1 | 12/2002 | Cosman |
| 2003/0018232 A1 | 1/2003 | Elliott et al. |
| 2003/0028401 A1 | 2/2003 | Kaufman et al. |
| 2003/0112922 A1 | 6/2003 | Burdette et al. |
| 2003/0144813 A1 | 7/2003 | Takemoto et al. |
| 2003/0153825 A1 | 8/2003 | Mooradian et al. |
| 2003/0182072 A1 | 9/2003 | Satoh et al. |
| 2003/0231790 A1 | 12/2003 | Bottema |
| 2004/0015075 A1 | 1/2004 | Kimchy et al. |
| 2004/0015176 A1 | 1/2004 | Cosman |
| 2004/0034301 A1 | 2/2004 | Falco |
| 2004/0092815 A1 | 5/2004 | Schweikard et al. |
| 2004/0146137 A1 | 7/2004 | Bruder et al. |
| 2004/0176925 A1 | 9/2004 | Satoh et al. |
| 2004/0184646 A1 | 9/2004 | Oosawa |
| 2004/0252870 A1 | 12/2004 | Reeves et al. |
| 2004/0260142 A1 | 12/2004 | Lovoi |
| 2005/0020917 A1 | 1/2005 | Scherch |
| 2005/0180544 A1 | 8/2005 | Sauer et al. |
| 2005/0251029 A1 | 11/2005 | Khamene et al. |
| 2006/0020195 A1 | 1/2006 | Falco et al. |
| 2006/0074292 A1 | 4/2006 | Thomson et al. |
| 2006/0093205 A1 | 5/2006 | Bryll et al. |
| 2006/0120608 A1 | 6/2006 | Luo et al. |
| 2006/0241443 A1 | 10/2006 | Whitmore et al. |
| 2006/0285641 A1 | 12/2006 | Scherch |
| 2006/0293583 A1 | 12/2006 | Saracen et al. |
| 2007/0015991 A1 | 1/2007 | Fu et al. |
| 2007/0038058 A1 | 2/2007 | West et al. |
| 2007/0055090 A1 | 3/2007 | Neustadter et al. |
| 2008/0039713 A1 | 2/2008 | Thomson et al. |
| 2008/0064953 A1 | 3/2008 | Falco et al. |
| 2008/0219405 A1 | 9/2008 | Falco et al. |
| 2008/0292194 A1 | 11/2008 | Schmidt et al. |
| 2009/0003523 A1 | 1/2009 | Raanes et al. |
| 2009/0093716 A1 | 4/2009 | Deischinger et al. |
| 2009/0110145 A1 | 4/2009 | Lu et al. |

FOREIGN PATENT DOCUMENTS

| | | |
|---|---|---|
| CA | 2621741 A1 | 3/2007 |
| EP | 0647457 A1 | 4/1995 |
| EP | 951697 A1 | 10/1999 |
| EP | 1304960 A1 | 5/2003 |
| EP | 1426806 A2 | 6/2004 |
| EP | 1757228 A1 | 2/2007 |
| FR | 2778574 A1 | 11/1999 |
| JP | 2006000220A A | 1/2006 |
| WO | WO-9902074 A1 | 1/1999 |
| WO | WO-99/06644 | 2/1999 |
| WO | WO-99/26534 | 6/1999 |
| WO | WO-99/27839 | 6/1999 |
| WO | WO-0105316 A1 | 1/2001 |
| WO | WO-0209588 A1 | 2/2002 |
| WO | WO-03/076003 | 9/2003 |
| WO | WO-2006051523 A2 | 5/2006 |

OTHER PUBLICATIONS http://www.acmp.org/meetings/hershey_2001/highlights/benedict.pdf.

Aoki, Y. et al. An Integrated Radiotherapy Treatment System and its Clinical Application, Radiation Medicine, vol. 5, No. 4, pp. 131-141, 1987.

Besl et al., A Method for Registration of 3d Shapes, IEEE Transactions on Pattern Analysis and Machine Intelligence 14(2):239-256 (1992).

Bijhold, J. et al. Fast evaluation of patient set-up during radiotherapy by aligning features in portal and simulator images, Phys. Med. Biol., 1999, vol. 36, No. 12, pp. 1665-1679.

Bijhold, J. Three-dimensional verification of patient placement during radiotherapy using portal images, Med. Phys. 20 (2), Pt. 1, Mar./Apr. 1993. pp. 347-356.

Boctor, et al., A Rapid Calibration Method For Registration and 3D Tracking Of Ultrasound Images Using Spatial Localizer, Proceedings of the SPIE (2003).

Booth, Modelling the impact of treatment uncertainties in radiotherapy, University of Adelaide, Mar. 2002), Section 2.4 (<http://thesis.library.adelaide.edu.au/uploads/approved/adt-SUA20020816.175301/public/03chapter2.pdf>.

Boyer, A. A review of electronic portal imaging devices (EPIDs), Med. Phys. 19 (1), Jan./Feb. 1992 pp. 1-.

Brujic et al., Analysis of Free-Form Surface Registration, International Conference on Image Processing, pp. 393-396 (1996).

Brunie L. et al. Pre- and intra-irradiation multimodal image registration: principles and first experiments, Radiotherapy and Oncology 29 (1993) pp. 244-252.

Christensen G. E., Inverse consistent registration with object boundary constraints, Biomedical Imaging: Macro to Nano, 2004, IEEE International Symposium on Arlington, VA, USA Apr. 15-18, 2004, Piscataway, NJ, USA, IEEE (18 pages).

Cuadra, M.B. et al., Atlas-based Segmentation of pathological MR brain images using a model of lesion growth; Medical Imaging IEEE Transactions on, vol. 23, No. 10, pp. 1301-1314, Oct. 2004.

Cuisenaire, O., <http://www.tele.ucl.ac.be/PEOPLE/OC/these/node12.html,> Posted Oct. 5, 1999, Downloaded from the Internet on Aug. 10, 2004.

Cuisenaire, O., <http://www.tele.ucl.ac.be/PEOPLE/OC/these/node75.html,> Posted Oct. 5, 1999, Downloaded from the Internet on Aug. 10, 2004.

Cuisenaire, O., <http://www.tele.ucl.ac.be/PEOPLE/OC/these/node74.html,> Posted Oct. 5, 1999, Downloaded from the Internet on Aug. 10, 2004.

Czarnota G.J. et al. Ultrasound imaging of apoptosis: high-resolution non-invasive monitoring of programmed cell death in vitro, in situ and in vivo, British Journal of Cancer (1999) 81(3), pp. 520-527.

Dubois et al. Intraobserver and Interobserver Variability of MR Imaging- and CT-derived Prostate Volumes after Transperineal Interstitial Permanent Prostate Brachytherapy, Radiology. 207(3):785-9 (1998).

Eggert et al., Simultaneous Registration of Multiple Range Views for Reverse Engineering, International Conference of Pattern Recognition, pp. 243-247 (1996).

Hanks et al., Clinical and Biochemical Evidence of Control of Prostate Cancer at 5 Years After External Beam Radiation, The Journal of Urology, vol. 154, 456-459 (1995).

Haralick et al., Pose Estimation From Corresponding Data Point, IEEE Transactions on Systems, Man, and Cybernetics, 19(6):1426-1446 (1989).

Hua et al., Development of a Semi-Automatic Alignment Tool for Accelerated Localization of the Prostate, Int. J. Radiation Oncology Biol. Phys., 55(3):811-823 (2003).

International Preliminary Report on Patentability for International Application No. PCT/CA2005/001106 dated Jan. 23, 2007.

International Preliminary Report on Patentability for PCT/CA2005/001428 dated Oct. 3, 2007 (1 page).

International Search Report for International application No. PCT/CA2007/001626 dated Jan. 3, 2008 (4 pages).

International Search Report for PCT/CA2005/001106 dated Nov. 15, 2005.

International Search Report for PCT/CA2005/001428 dated Nov. 16, 2005.

International Search Report for PCT/CA2005/01105 dated Oct. 27, 2005.

International Search Report for PCT/CA2006/001289 dated Oct. 30, 2006 (3 pages).

International Search Report for PCT/CA2006/001461 dated Nov. 30, 2006 (5 pages).

International Search Report for PCT/CA2007/000898 dated Jul. 12, 2007 (3 pages).

Jiang et al., *A New Approach to 3-d Registration of Multimodality Medical Images by Surface Matching*, SPIE vol. 1808 Visualization in Biomedical Computing pp. 196-213 (1992).

Leszczynski K W et al., "An Image Registration scheme applied to verification of radiation therapy" British Journal of Radiology British Inst. Radiol UK [Online] vol. 71, No. 844, Apr. 1998, ISSN: 0007-1285, retrieved from the Internet: url:http://bjr.birjournals.org/cgi/reprint/71/844/413.pdf. [retrieved on Nov. 10, 2009].

Lizzi, Frederic, et al., "Ultrasonic Spectrum Analysis of Tissue Assays and Therapy Evaluation," International Journal of Imaging Systems and Technology, Wiley and Sons, New York, vol. 8, No. 1, (Jan. 1, 1997), pp. 3-10.

Maurer C R et al., Registration of 3-D Images Using Weighted Geometrical Features, IEEE Transactions on Medical Imaging, IEEE Service Center, Piscataway, NJ, US vol. 15, No. 6, Dec. 1, 1996 (14 pages).

Meertens, H. et al. A method for the measurement of field placement errors in digital portal images, Phys. Med. Biol., 1990, vol. 35, No. 3, pp. 299-323.

Mencarelli, et al., "A Dosimetric Method to derive optimal couch corrections in the presence of anatomical deformations for H & N cancer," abstract, 2011, 2 pages.

Michalski et al., Three-Dimensional Conformal Radiation Therapy (3DCRT) for Prostate Cancer, Radiation Oncology Center, Mallinckrodt Institute of Radiology, Washington University Medical Center, St. Louis, Missouri (1996) <http://www.phoenix5.org/Infolink/Michalski/#3>.

Nagel, et al., "Online dose-guided setup correction protocol for hypo fractionated lung radiotherapy," abstract, 2009, 1 page.

Paskalev et al., Daily Target Localization for Prostate Patients based on 3-D Image Correlation, Phys. Med. Biol., vol. 49, pp. 931-939 (2004).

Pennec et al., A Framework for Uncertainty and Validation of 3-D Registration Methods Based on Points and Frames, International Journal of Computer Vision 25(3), 203-229 (1997).

Pito, A Registration Aid, International Conference on Recent Advanced in 3D Digital Imaging and Modelling, pp. 85-92 (1997).

Reinstein, L. et al. Radiotherapy Portal Imaging Quality, Report of AAPM Task Group No. 28, American Association of Physicists in Medicine by the American Institute of Physics, New York, 1988.

Robb, Three-Dimensional Visualization in Medicine and Biology. Book Chapter in: Handbook of Medical Imaging: Processing and Analysis, ed. Isaac N. Bankman, Academic Press, San Diego, CA, Chapter 42, pp. 685-71 (2000).

Robinson, Advances in Multi-Modal Data Analysis: The ANALYZE Software Environment, <http://www.ii.metu.edu.tr/~med-ii/makaleler/analyze_sw_enve.pdf>, 5 pages. Downloaded on Aug. 10, 2004.

Search Report for European Patent Application No. 06790638.8, mailed Apr. 23, 2010 (7 pages).

Simpson, R.G. et al. A 4-MV CT scanner for radiation therapy: The prototype system. Med. Phys. 9(4), Jul./Aug. 1982, pp. 574-579.

Soffen E.M. et al. Conformal static field radiation therapy treatment of early prostate cancer versus non-conformal techniques: A reduction in acute morbidity. Int J Radiat Oncol Biol Phys, 24: 485-488 (1992).

Supplementary European Search Report for PCT/CA2005001106_RNM-003PC_ dated Nov. 10, 2009, 6 pages.

Supplementary European Search Report dated Oct. 25, 2010 (5 pages).

Supplementary Partial European Search Report for EP Application No. 5763463, dated Nov. 30, 2009, 7 pages.

Supplementary European Search Report dated Oct. 30, 2008 for European Patent Application No. 05788508.9/PCT/CA2005001428.

Swindell, W. et al. Computed tomography with a linear accelerator with radiotheraphy applications, Med. Phys. 10(4), Jul./Aug. 1983, pp. 416-420.

Thayananthan, A. et al., <http://mi.eng.cam.ac.uk/~bdrs2/papers/thayananthan_cvpr03.pdf>, pp. 1-8. Downloaded from the Internet on Aug. 10, 2004.

Tome et al., Commissioning and Quality Assurance of an Optically Guided Three-dimensional Ultrasound Target Localization System for Radiotherapy, Med. Phys., 29(8):1781-1788 (2002).

Troccaz, J. et al. Conformal external radiotherapy of prostatic carcinoma: requirements and experimental results, Radiotherapy and Oncology 29 (1993) pp. 176-183.

Troccaz., J et al. Patient Setup Optimization for External Conformal Radiotherapy, Journal of Image Guided Surgery, 1, pp. 113-120 (1995).

Van de Geijn, J. et al. A Graticule for Evaluation of Megavolt X Ray Port Films, Radiation Oncology Biology Physics, Nov. 1982, vol. 8, No. 11 pp. 1999-2000.

Written Opinion for PCT/CA2005/001106 dated Nov. 15, 2005.

Written Opinion of the International Search report for PCT/CA2005/001105 dated Oct. 27, 2005.

Written Opinion of the International Searching Authority for International application No. PCT/CA2007/001626 dated Dec. 21, 2007 (7 pages).

Written Opinion of the International Searching Authority for PCT/CA2005/001428 dated Nov. 8, 2005 (6 pages).

Written Opinion of the International Searching Authority for PCT/CA2006/001289 dated Oct. 30, 2006 (6 pages).

Written Opinion of the International Searching Authority for PCT/CA2006/001461 dated Dec. 8, 2006 (5 pages).

Written Opinion of the International Searching Authority for PCT/CA2007/000898 dated Jul. 23, 2007 (6 pages).

Zhang, Iterative Point Matching for Registration of Free-Form Curves and Surfaces, International Journal of Computer Vision, 13(2):119-152 (1994).

Zitova, B. et al., Image Registration Methods: A survey, Image and Vision Computing, Elsevier, Guildford, GB, vol. 21, No. 11, Oct. 1, 2003 (24 pages).

* cited by examiner

METHODS AND SYSTEMS FOR GUIDING CLINICAL RADIOTHERAPY SETUPS

CROSS-REFERENCE TO RELATED APPLICATIONS

This application claims priority to and the benefits of U.S. provisional patent application Ser. No. 61/058,049, filed on Jun. 2, 2008, the entire disclosure of which is incorporated herein by reference

FIELD OF THE INVENTION

This invention relates generally to methods and systems for improving setups in radiotherapy.

BACKGROUND OF THE INVENTION

External-beam radiotherapy for breast cancer is typically provided using opposing tangential fields, which deliver a uniform dose to the entire affected breast. The primary treatment is given over a number of sessions, and is often followed by additional boost sessions. The boost sessions are typically delivered with an electron beam, which limits treatment to the primary lumpectomy site.

Unlike photons, the intensities of which decrease exponentially as the photons travel through a patient, an electron beam deposits most of its energy dose within a fixed, finite range based primarily on the energy of the beam. Thus, a single electron beam can be used to treat superficial lesions while sparing underlying healthy tissues. Electron-beam treatments are typically delivered using electron cones of various sizes and shapes that may be attached to the collimator of a linear accelerator (LINAC), and which collimate the electron beam very close to the patient surface. The cones may have standard geometric shapes, such as circles or squares of various sizes, or an arbitrary shape can be custom-made for a given patient. In some instances, a lead sheet having an opening that defines the aperture of the beam is placed directly on the patient's skin.

Electron-beam treatment plans usually involve a fixed source-to-skin distance (SSD). For breast boosts, an SSD of 100 cm is typical, as this is the same distance from the beam source to the isocenter of most LINACS. As a result, the LINAC isocenter, and hence the intersection of any wall lasers being used to align the patient with the LINAC, lies on the surface of the patient's skin. This is in contrast to many photon treatments, which are planned such that the isocenter is near the center of the treatment volume within the patient, as opposed to on the patient's skin.

For a breast boost, the electron field ideally covers the tumor bed and the surgical path leading from the tumor bed to the surgical scar, plus a 1-2 cm margin. In addition, it is preferable to avoid the areola. Electron breast boosts may be simulated either using clinical or CT planning performed directly on the linear accelerator, or on a conventional simulator. In such simulations, a physician uses the lumpectomy scar and palpation to determine the location of the lumpectomy site relative to the patient's skin. A cut-out, usually made of CERROBEND, is designed to cover the region of interest on the patient's skin. The angles of the beam gantry and the couch on which the patient reclines are physically adjusted such that the beam is substantially perpendicular to (i.e., en face) the patient's skin. The appropriate electron energy is then chosen so that the beam covers the depth of the tumor bed, which may be found from post-surgery ultrasound scans, for example. The greater the energy of the electron beam, the deeper the electrons will penetrate. The correct number of "Monitor Units," a calibrated measure of LINAC output, required to deliver a percentage of the prescribed dose at a given depth is calculated from tabulated beam data.

One weakness of clinical planning is that the actual position of the cavity is not explicitly taken into account. For this reason, in some institutions the simulation is performed using computed tomography (CT-SIM). One such technique uses radio-opaque wire placed around the surgical scar, and sometimes around the areola, prior to the acquisition of a CT scan. Thus the scar and the lumpectomy site, as seen on the CT scan, can be used to design the electron field. Energy and monitor units are calculated using treatment-planning software.

Once the plan (clinical or CT-based) is finished, the goal is to deliver radiation treatment according to the plan for each treatment session, or fraction thereof. For each fraction, the setup may be adjusted so that the field covers the same skin surface area as planned, using a preferred source-to-skin distance (SSD), with the beam oriented en face. These adjustments are often necessary because it is difficult to reposition the breast in exactly the same way from day to day since the breast is not a rigid structure, and consequently its shape, size and position can vary daily. Therefore, the setup can be adjusted by changing couch position, collimator angle, gantry angle and/or couch angle to take into account external features.

In making adjustments, it is possible to take into account not only external landmarks, but also internal anatomy. Physically moving and/or rotating the couch, gantry and collimator to properly orient the patient can be cumbersome, however, primarily due to the constraint of maintaining the planned SSD. Therefore, greater automation would be beneficial in utilizing internal and/or external landmark information to adjust patient setup, particularly where the planned SSD is taken into account.

SUMMARY OF THE INVENTION

Embodiments of the present invention provide systems and methods for incorporating internal and external anatomical features of a patient and radiation-beam parameters into radiation-treatment treatment and/or planning regimens. A tracked tool or instrument may be used to illustrate a desired beam entry point and/or beam angle, which in turn facilitates the determination of the desired gantry and couch angles as well as couch positions. An SSD may also be determined and, in some cases, enforced prior to or during treatment.

In a first aspect, various embodiments of the invention provide methods for establishing radiation beam parameters for delivery of radiotherapy treatment to a patient using a radiotherapy treatment device. The method includes the steps of orienting a wand with respect to the patient to establish a beam entry point and acquiring positional parameters characterizing the wand's position (such as a tip position and/or an orientation) with respect to a room coordinate system. A beam angle is defined according to the room coordinate system that is consistent with the beam entry point.

In some implementations, images of internal anatomical features of the patient may be obtained (using, for example, CT scanning, MRI, and/or ultrasound devices) and/or external anatomical features of the patient can be digitized as images. The patient's internal and/or external anatomy may then be displayed within the beam area corresponding to the defined beam angle such that the anatomical features are viewed along with the desired entry point and treatment path.

In some embodiments, the tool is a wand-like instrument having a shaft and a well-defined tip, and one or more affixed markers that can be tracked by a tracking device. This tracking device, through known calibration techniques, can determine the position of the tip, as well as the orientation of the wand, in a "room coordinate system" of a planning room or a treatment room. The positions and orientations of the wand are preferably output to a computer application, with an interactive display in the room.

The orientation of the wand may be used to define a beam angle—that is, the user orients the wand relative to the patient's external anatomy to establish a desired beam trajectory relative to the patient. In practice, this hypothetical angle can be converted to gantry and couch angles of a LINAC by a computer application so that the actual beam angle during treatment conforms to the hypothetical angle established using the wand.

In some embodiments, the wand tip is used to digitize a hypothetical beam entry point on the patient's surface. This is particularly useful for fixed SSD beam setups, where a given point on the patient's skin must be set up at a predetermined distance from the radiation source. The beam entry point can be converted to physical manipulations—e.g., translations and/or rotations of the couch, gantry and/or collimator—required to set up the patient to the digitized beam entry point, so the actual beam entry point corresponds to the hypothetical point established using the wand. In this way, physical geometry of the patient setup matches the geometry defined by the wand tool. The necessary physical manipulations can be performed automatically by transferring parameters specifying the movements to electromechanical controllers, or manually by providing these parameters as movement instructions that the therapist may carry out. Couch motion and/or rotation can also be facilitated by affixing trackable markers to the treatment couch, and tracking these markers while the couch is moved. A computer program tracking the markers can guide the therapist as physical manipulations are carried out so that the correct position and angle are attained. In some cases, the planned couch and gantry angles may not be optimal on a given day due, for example, to varying patient anatomy or setup position. For example, in breast setups, the size, shape and position of the breast and its internal targeted structures can vary from day to day. In these cases, the wand can be used to calculate new gantry and couch angles for the patient. In some cases this is done in combination with the determination of the beam entry point.

The beam entry point may be calculated automatically from surface information. For example, surface information can be acquired by sampling multiple points on the patient's body surface with the wand tip, or by using a three-dimensional surface camera. Alternatively, surface data can be extracted from a patient image.

In another aspect, embodiments of the invention provide a system for establishing radiation beam parameters for treatment of a patient. The system includes a tool and a tracking device for sensing positional information of the tool (e.g., tip position, orientation) with respect to the patient and to establish a beam entry point. The system also includes a processor for characterizing a beam trajectory through the beam entry point with respect to a room coordinate system and defining a desired beam angle consistent with the beam entry point.

In some embodiments, the tool further comprises one or more optical tracking sensors identified by the tool tracking device, which may use optical and/or radio-frequency modalities (as well as others) to locate and track the tool as it is manipulated about the patient. The system may also include one or more registers for storing image data corresponding to internal and/or external anatomical features of the patient, and in some implementations the imaging devices for obtaining the image data. In some cases, some images may be obtained by tracing external anatomical features using the tool. The system may also include a display device for displaying the internal and/or external anatomical features of the patient within a beam's eye view of a radiation treatment device, wherein the beam's eye view is oriented along the desired beam angle. The display may also provide additional beam information, such as a beam aperture, a dose information, and an electron beam depth.

A controller may be used to determine couch and/or gantry movement parameters, and direct the movement of either such that a radiation beam may be delivered to the patient along the desired beam angle. In certain cases, the processor correlates the beam entry point with a desired source-to-skin distance. In such instances, the tool orientation may also define a current source-to-skin distance, and the controller may further determine couch and/or gantry movement parameters for shifting the current source-to-skin distance to a desired source-to-skin distance.

BRIEF DESCRIPTION OF THE DRAWINGS

The foregoing and other objects, features, and advantages of the present invention, as well as the invention itself, will be more fully understood from the following description of various embodiments, when read together with the accompanying drawings, in which.

DETAILED DESCRIPTION

Figure 1:
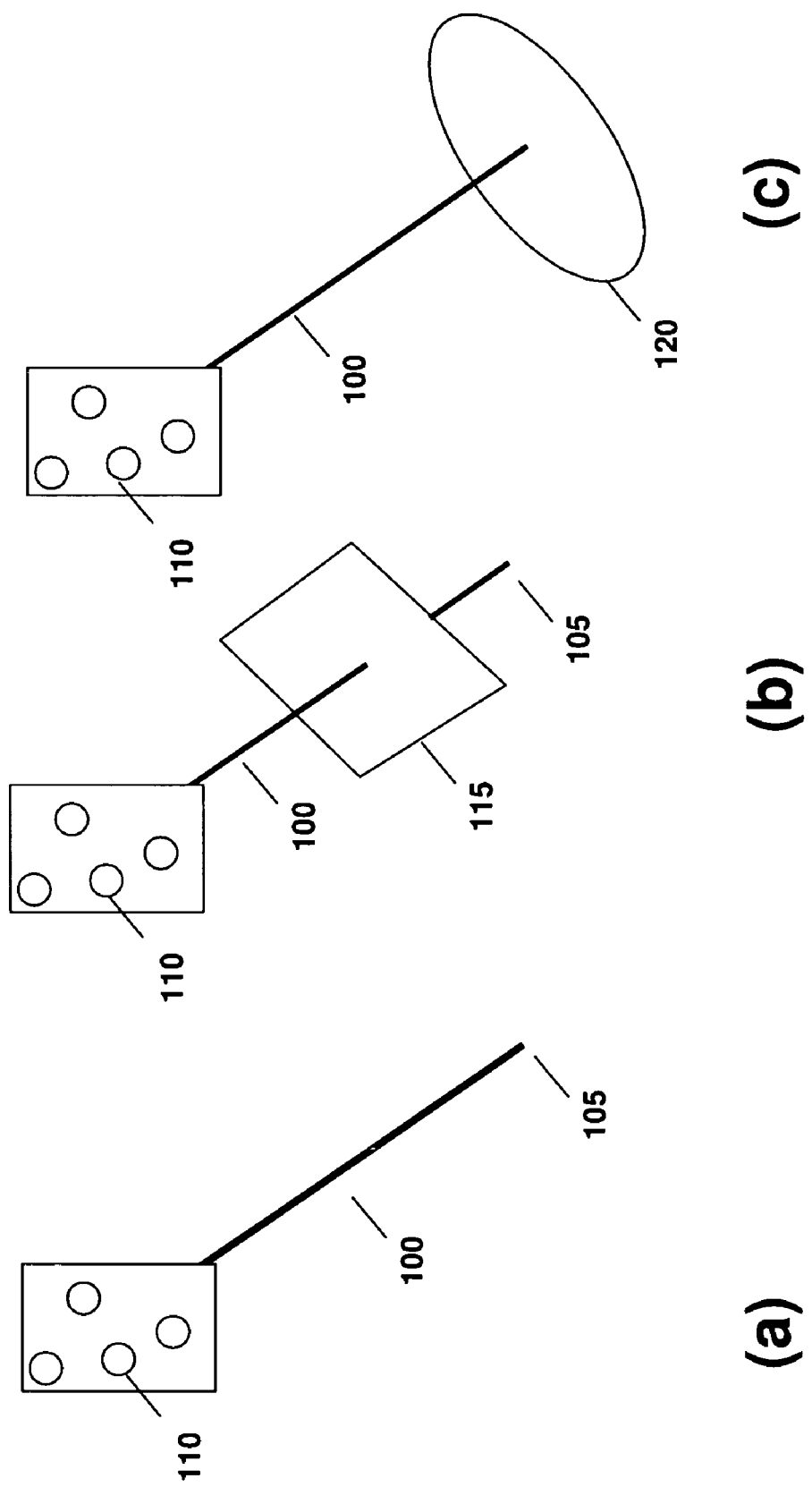
FIGS. 1(a)-1(c) illustrate a wand tool which may be used to guide radiation beams in accordance with various embodiments of the invention.

FIG. 1 illustrates an exemplary wand tool in accordance with various embodiments of the invention. As shown in FIG. 1(a), the wand has a shaft 100 and a tip 105 that is preferably well-defined, for example, as a sharp, blunt or ball tip. In some embodiments, an array of markers 110 are affixed to the pointer. The markers 110 can be detected by a conventional optical tracker in real-time. The markers can be tracked either individually or as a preconfigured shape configuration, which defines a position and orientation in space. The position and orientation are calibrated so that the position of the tip 105, the orientation of the shaft 100, long-axis rotation and shaft rotation about its long axis, can be calculated at any given time as the wand is moved. Examples of markers include passive infrared reflectors, or active infrared emitters, which can be tracked by an optical camera or cameras such as the POLARIS family of cameras. Other types of trackers, such as magnetic or radio-frequency devices, can also be used.

FIG. 1(b) shows the addition of a plate 115, which is preferably transparent to allow the user to more easily judge whether or not a surface is perpendicular to the wand tool (i.e., whether it is en face to the skin surface). The plate 115 may be removable so that the wand tool can be more easily used for other functions where the user needs a clear view of the tip 105, such as digitizing points on a surface. In some cases, the distance between the plate 115 and the tip 105 can correspond to a physical distance related to the radiation device, such as the distance between the applicator and the skin. In another variation, shown in FIG. 1(c), a plate 120 (illustrated with a circular shape) is affixed at the end of the rod 100. The plate 120 can make evaluating en face angles easier, but at the expense of losing precise awareness of the position of the tip 105. This plate 120 may also be removable, or adjustable up and down the shaft.

Calibration of the wand tool with respect to the room coordinate system may be more accurate when the mechanical geometry of the markers is known relative to the axis of the tool and its tip, e.g., from a precise CAD geometry. The relationship between the tool axis and tip to the pattern recorded by the tracker can then be calculated. If the geometry is not known accurately enough, or if there is too much variability in manufacturing the tool, appropriate calibration can be performed using other methods known in the art. For example, a snapshot of the markers can be acquired with the tracker to establish the marker pattern. Mechanical rotations of the tool about the tip, along pre-established trajectories, during marker acquisition by the tracker can then be used to mathematically extract the transformation between the tip and the marker pattern. Similar established motions along or about the axis of the tool can also be used to define the transformation between the axis and the pattern. Once calibration is complete, the tip position and wand orientation can be converted to room coordinates as is commonly done in the art.

In some embodiments, aspects of the beam defined by the wand are used for treatment planning purposes. The beam or beams are defined with the patient present, using the wand, and, in some cases, taking into account external and/or internal features. This beam definition is sent to a treatment planning computer, or in some cases to an in-room computer associated with the LINAC, to determine proper patient positioning and/or to calculate dose distributions. Having the patient present for design of treatment beams, rather than designing them exclusively on pre-acquired images, can be of particular importance for clinical setups, where the physician may want to take visible and/or palpable information into account in the beam design. The ability to design a beam directly on the patients' skin, for planning or treatment purposes, is especially useful for electron beams which are generally kept en face. The beam can be designed to target the appropriate structures while ensuring visually that it is en face.

One exemplary application of the techniques described herein involves clinical planning of a breast electron boost beam, which is typically carried out directly on a LINAC or on a conventional simulator. Critical treatment parameters include the beam angle (defined by a gantry and couch rotation) and beam entry point required to target the visible external information, each determined while maintaining an en face beam direction and a fixed source-to-skin distance (SSD) (together referred to as "beam alignment"). Internal image information may also be considered when determining beam alignment. Other information which can be obtained is beam depth and energy, collimator rotation and an electron cut-out shape.

Typically, the user orients the wand relative to the patient's skin. For example, the user may align the axis of the wand so that it is en face. In certain embodiments, an image of the patient is acquired prior to use of the wand (as described, for example, in U.S. patent application Ser. No. 11/852,492, filed on Sep. 10, 2007, the entire disclosure of which is hereby incorporated by reference) and used as a guide. As the user moves the wand about the patient, the tracked wand coordinates—relative to the patient or room coordinate system—are keyed to the coordinates of internal images of the patient's anatomy, so that elements of the internal anatomy (e.g., a lesion, tumor bed or cavity) are displayed and updated as the position and orientation of the wand changes. The internal images may have been obtained during the same planning or treatment session using, for example, CT scanning, cone-beam CT, MRI, and/or ultrasound devices.

In some embodiments, turning the wand about its axis simulates a collimator rotation, which is calculated along with the couch and gantry parameters. In other embodiments, the collimator may be rotated on-screen after the gantry and couch angles have been calculated using the wand. Once the wand position is aligned according to a desired beam trajectory relative to the patient's anatomy, the position of the patient may be adjusted such that the actual treatment device beam (which, in some cases may be fixed) corresponds to the desired beam trajectory.

In other embodiments, the system may be used to define a beam digitally for future dosimetric or geometric planning purposes. This can be done, for example, in a CT-SIM room, a conventional simulator, or on the LINAC. The orientation of the wand used to define the beam can then be converted to beam orientation and/or couch and gantry angles, and sent electronically to a treatment planning system, e.g., via the DICOM transfer protocol. This approach, which effectively combines elements of both CT planning and clinical planning, is of particular use in the CT-SIM room, where it can be difficult to visualize different beam orientations directly on the patient.

In practice, the internal anatomy is displayed on an interactive monitor in either the "beam's-eye view" or in a plane perpendicular to or passing through the axis of the beam (i.e., along the depth direction). In addition to or instead of displaying actual image gray-scale information, surfaces or contours of external anatomical landmarks (e.g., scars, markings, etc.) can be displayed relative to the wand. Where external points or contours of interest on the patient's skin are digitized, the tip of the wand may be used to identify or outline the contours, which are then simultaneously displayed on the interactive monitor along with the internal features.

In some embodiments, the interactive display updates a beam's-eye-view plane perpendicular to the wand's direction, along with the treatment aperture of the radiation beam. This facilitates visualization of which internal and external structures fall within the radiation beam. The depth direction may be shown separately or in combination with the beam's-eye view. This is particularly useful for electron treatments, where the depth of the electron beam can be displayed to ensure proper coverage of the involved anatomy. Dosimetric information can be displayed relative to the anatomy as well, in any view.

In some embodiments in which the radiation treatment is delivered in multiple fractions, the process is divided into two steps. In the first step, the cavity position identified in the pre-treatment image is aligned (manually or automatically) to its position at treatment time by conventional image-alignment software and displayed to the user. In the second step, the user employs the wand tip to digitize the beam entry point (corresponding to the beam central axis on the patient's skin) with the image of the cavity. This can be done by displaying the real-time position of the wand tip on the display relative to the virtual beam's-eye view (i.e., the beam view relative to the virtual cavity alignment). The user then moves the wand such that its tip lies on the patient's skin surface and within a specified tolerance from the central axis of the beam's-eye view on the display. The patient shifts required to align the patient to the beam can then be calculated from the cavity shift and beam entry point. Using the example above in which a breast electron boost beam is delivered using a LINAC having a fixed beam, the position of the patient may be moved by adjusting the physical alignment of a couch relative to the LINAC using multiple (e.g., typically three or as many as six) degrees of freedom.

Figure 2:
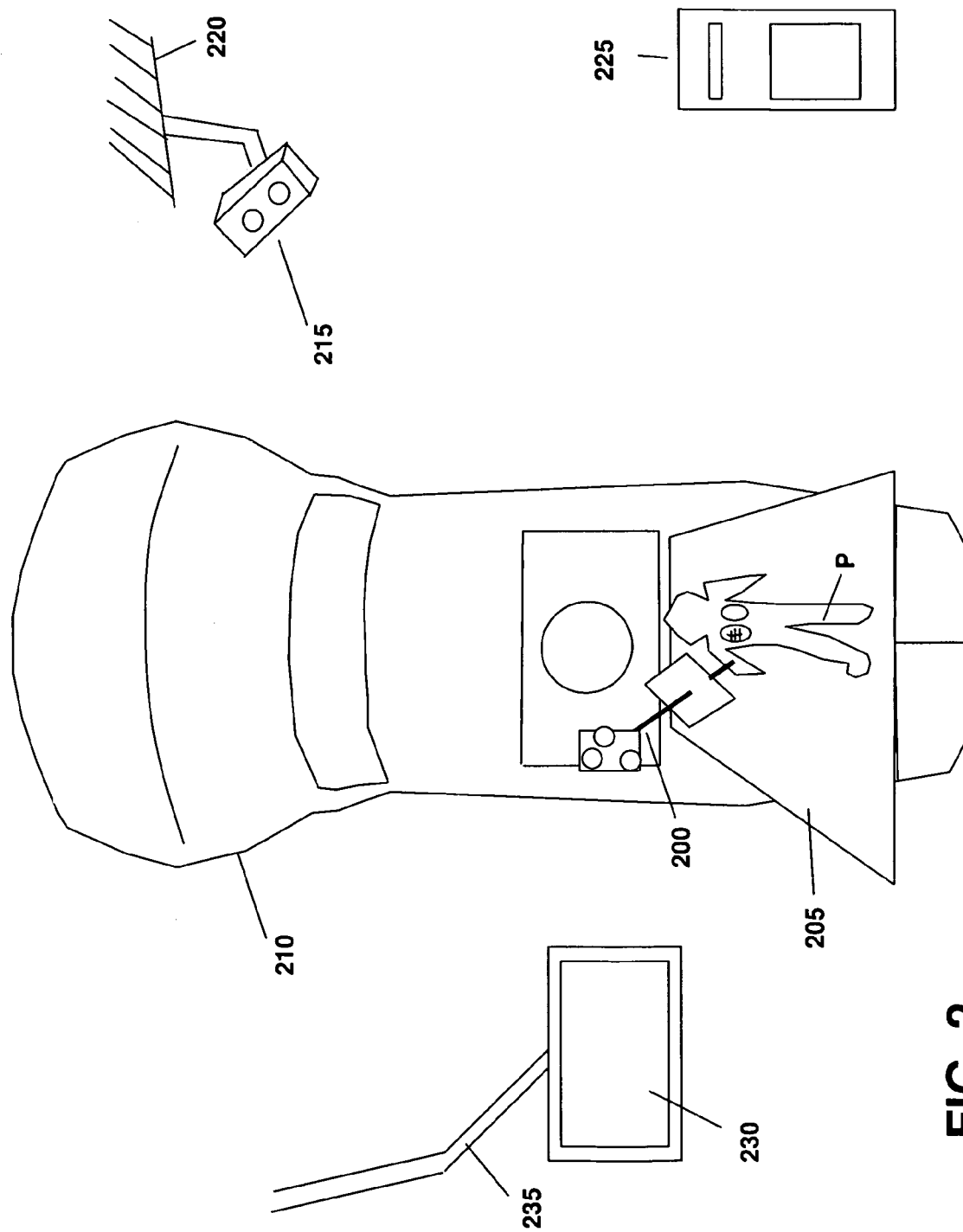
FIG. 2 illustrates the administration of radiation therapy in accordance with various embodiments of the invention.

FIG. 2 shows a patient P lying on a treatment couch 205 (or other patient-support assembly) of a linear accelerator 210, in an initial position. This initial position may be arbitrary, or the patient may have markings (such as tattoos or ink marks) that are aligned to a room coordinate system, which in some cases may be defined by a set of perpendicular lasers. The wand tool 200 is tracked by a tracker 215 attached to the ceiling 220 of the treatment room. Alternatively, the tracker may be attached to another fixed and known position in the room, such as a wall, beam and/or fixture. The tracker can also be mobile if there is a fixed object or tool that can be used to define a patient coordinate system. The output of the tracker 215 is transmitted (using wired or wireless methods) to a computer 225 having an associated visual display 230. Using suitable calibration data, the computer 225 processes the output to derive the orientation of the wand axis and the position of the wand tip in the room coordinate system. The computer 225 may in some instances be integrated directly into the console of the visual display 230, or can be located outside the treatment room, connected to or communicating wirelessly with the display 230. The visual display 230 can be cart-based but is preferably mounted to a swing arm 235 attached to the ceiling, such that the user (e.g., a radiation therapist, a dosimetrist, a medical physicist or a radiation oncologist) can move the visual display 230 to any convenient location.

In some embodiments, the physician may use a marking tool to draw a closed shape on the patient's skin, typically surrounding the patient's scar, which corresponds to the desired treatment aperture. The user then digitizes this shape by tracing the tip of the wand tool around the contour. The computer 225 acquires the traced shape via the tracking system 215 as a discrete set of points with known locations in the room coordinate system. Alternatively, another pointer tool or digitizing device such as a camera can be used to digitize the points represented by the drawn shape, but using the wand tool directly is more convenient than using two separate tools.

The user then moves the wand tool such that the tip is at the desired entry point of the beam on the patient's surface, typically close to the center of the drawn aperture, and ensures that its axis is en face to the patient's skin. Once the user establishes the proper position and orientation of the wand tool relative to the patient, the computer 225 captures the position and orientation of the wand (e.g., in response to pressing a button on the touch screen 230 or on the wand itself indicating that the user is satisfied with the wand position, or in response to a stability criterion indicating the user has stopped moving the wand). The tip of the wand corresponds to the desired beam entry point, and the orientation of the wand defines the beam direction. Based on the mechanical movement constraints and capabilities of the couch and the gantry, which are programmed into the computer 225, the computer calculates the couch shifts required to align the patient to the beam entry point to a defined SSD, and the couch and gantry rotations required so that the direction of treatment beam will follow the captured wand orientation. An SSD of 100 cm is usually used for electron boost treatments. The computer may be programmed to recognize wand orientations that correspond to impossible gantry and couch movements, and to cause a warning to be displayed on the screen 230 in such cases.

Figure 3:
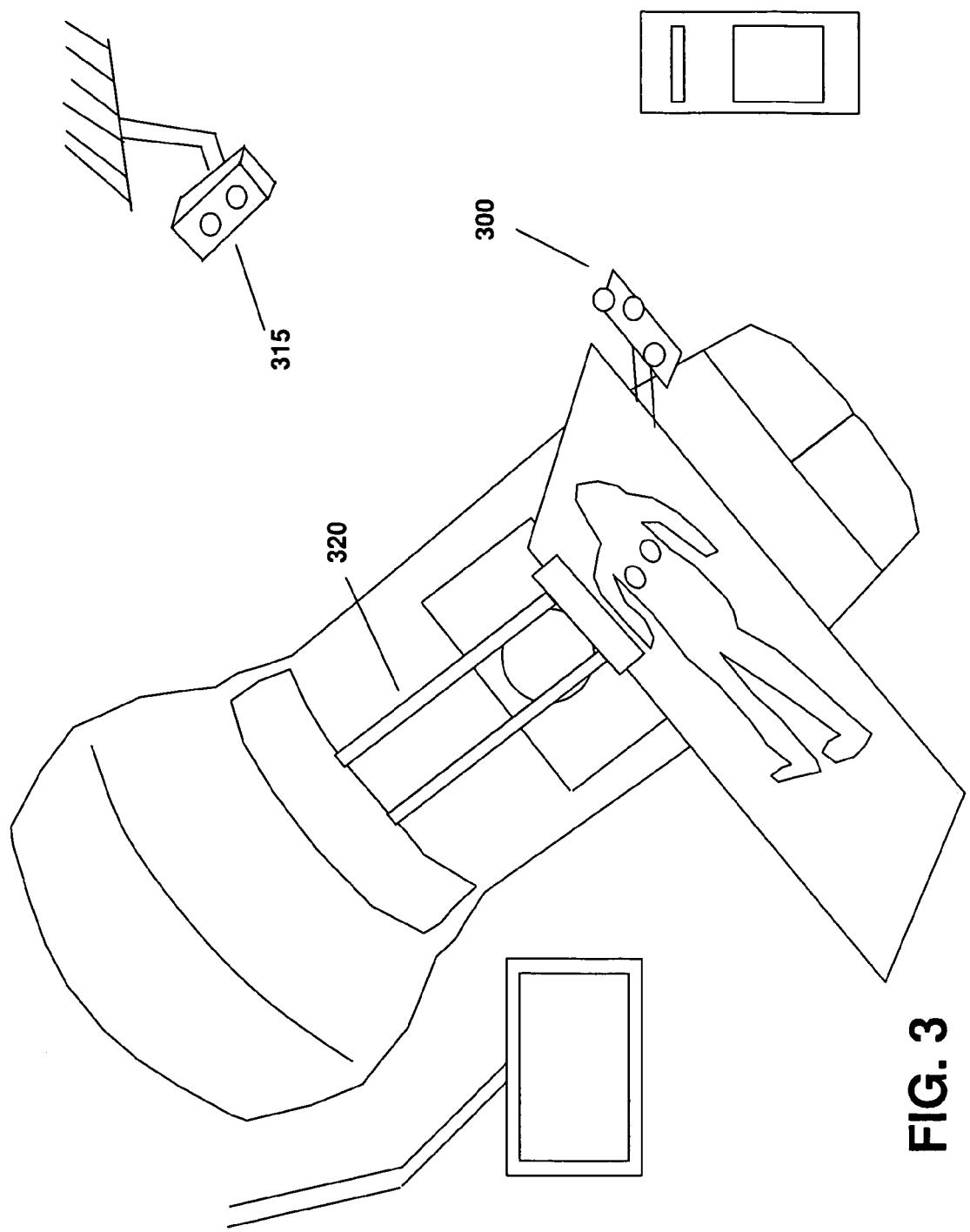
FIG. 3 illustrates adjustments being made to the orientation of a radiation delivery system in accordance with various embodiments of the invention.

Assuming the beam direction established by the wand position and orientation can be accommodated by the couch and gantry, the necessary movements are executed as shown in FIG. 3. In some embodiments, this is done by transferring the couch and gantry parameters directly to the computer driving the couch and LINAC. In other embodiments, the user moves the gantry and couch manually. The manual couch motion can be simplified by mounting an attachment 300 to the couch which has active or passive markers affixed to it. As the user moves and/or rotates the couch, the camera 315 tracks the motion and feeds this information back to the computer 225, which is programmed to assist the user—e.g., indicating how much to move and rotate the couch until the correct parameters are achieved.

For ease of use, the beam entry point may be digitized with the pointer tip separately from the beam orientation. In other embodiments, the beam direction may be determined by other means, and only the beam entry point, along with associated calculated couch shifts, is determined with the wand.

In alternative embodiments, instead of digitizing the beam entry point with the wand, it is calculated from digital surface data obtained from the patient. For example, surface information can be acquired by sampling multiple points on the patient's surface with the wand tip, or by using a three-dimensional surface camera. If an image (such as a CT) of the patient is acquired which encompasses the patient's skin, the surface information can be extracted from the image for this purpose using manual or automatic contouring algorithms.

If desired, the digitized cut-out information may be printed to enable correct machining of the treatment field aperture, often referred to as an electron cut-out. The digitized cut-out may also be sent electronically to a milling machine, which creates the cut-out. At any time, the electron applicator 320 may be affixed to the LINAC. If the cut-out exists in the clinic, which will usually be the case if it is simple such as a standard square or circle, it can be affixed to the applicator and the treatment delivered; otherwise, treatment will usually be delayed to a succeeding treatment session.

Figure 4:
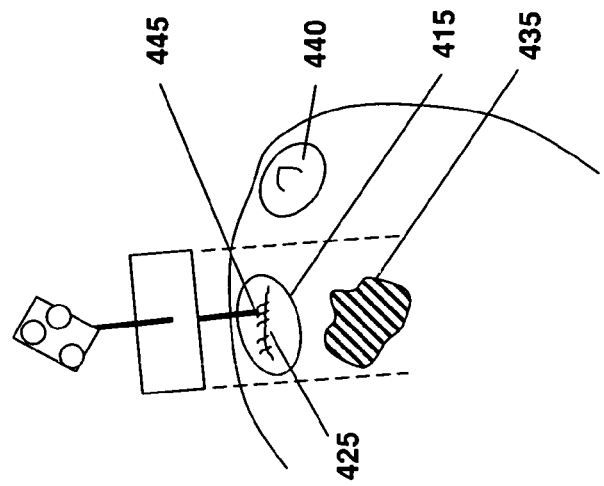
FIG. 4 illustrates a treatment being delivered to a patient and a corresponding display of the treatment in accordance with various embodiments of the invention.
Figure 4:
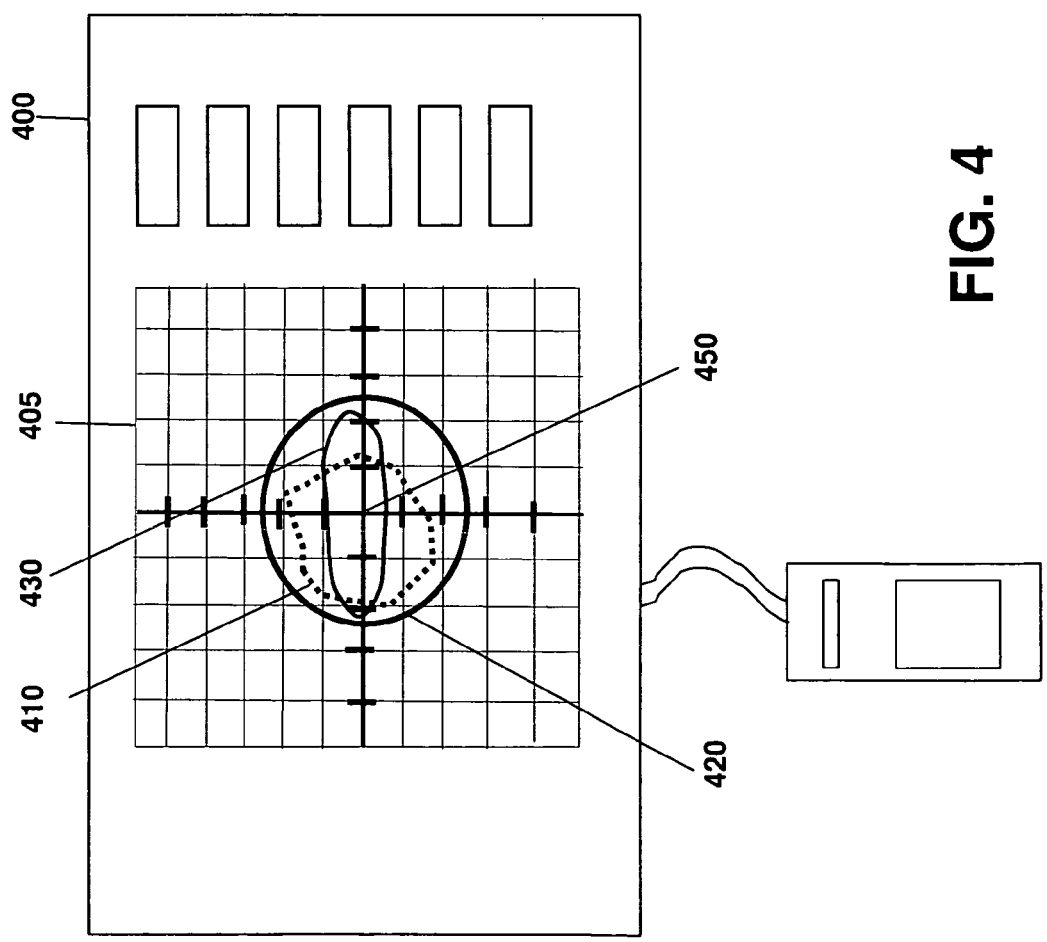

In addition to directly digitizing the aperture from markings drawn on the patient's skin, the wand tip or other digitizing tool may also (or alternatively) be used to digitize anatomic surface structures (such as scar and areola) directly, while the patient P is in the initial position. As shown in FIG. 4, the user interface 400 can then display the digitized information in the beam's-eye view 405 of the wand as it is moved about the patient, allowing the user to determine beam entry position and/or beam angle directly on the user interface. The cut-out can then be defined directly on the screen as well.

Typically, one or more images are acquired with the patient P in the initial position. For example, a three-dimensional ultrasound, a cone-beam CT image, MRI, or multiple two-dimensional x-ray projection images can be obtained. Anatomical information, such as the lumpectomy cavity and chest wall, can then be segmented from these images manually or using conventional algorithms. The projection of the extracted surfaces 410 can then be displayed in real-time on the visual display 400 along the beam's-eye view defined by the wand. This allows the beam entry point and beam direction, as well as the cut-out shape, to be determined based on both external and internal anatomical features.

FIG. 4 shows one embodiment where the cut-out drawn on the skin 415 is digitized and shown as 420 on the visual display 400 within the beam's-eye view 405. The contour of the scar 425 is also digitized and shown as a projection 430 along the beam's-eye view. The internal anatomy of interest 435 is segmented and its projection 410 is shown in the beam's-eye view. For breast treatments, the areola 440 may also be digitized and included in the beam's-eye view. The tip of the wand 445 is positioned such that it corresponds to the beam entry point, and hence the center of the beam's-eye view 450. The wand orientation and beam alignment corresponding to the current gantry angle and couch position are updated in the visual display. The computed couch positions may be updated as the wand is moved to indicate which displacements will result in correct alignment of the patient such that the digitized beam entry point is at the correct SSD.

The invention can be used for subsequent treatment fractions as well as the initial treatment or simulation. In this case the cut-out is already known from the first treatment session or simulation, but adjustments must ordinarily be made in the beam angle and position to compensate for daily changes in patient setup, and deformations of the anatomy to be treated. In this case, the planned cut-out may be superimposed (as shown at 420) on the projection of internal and external anatomical information in the beam's-eye view as the wand is moved about the patient.

In some embodiments related to treatment fractions, it may be more practical to avoid adjusting the couch and gantry angles for each treatment fraction, and instead re-align the beam relative to the patient anatomy using only couch displacements. In this case, the user can employ the wand to define the beam entry point relative to internal and/or external anatomy, and the real-time beam's-eye view is fixed at the planned couch and gantry values. If the user is not able to determine an appropriate setup based on beam entry point alone, the wand can be used to determine daily couch and gantry angles as well. In this regard, it may be useful to display not only the current internal and external anatomy relative to the wand, but the anatomy at time of planning as well.

Figure 5:
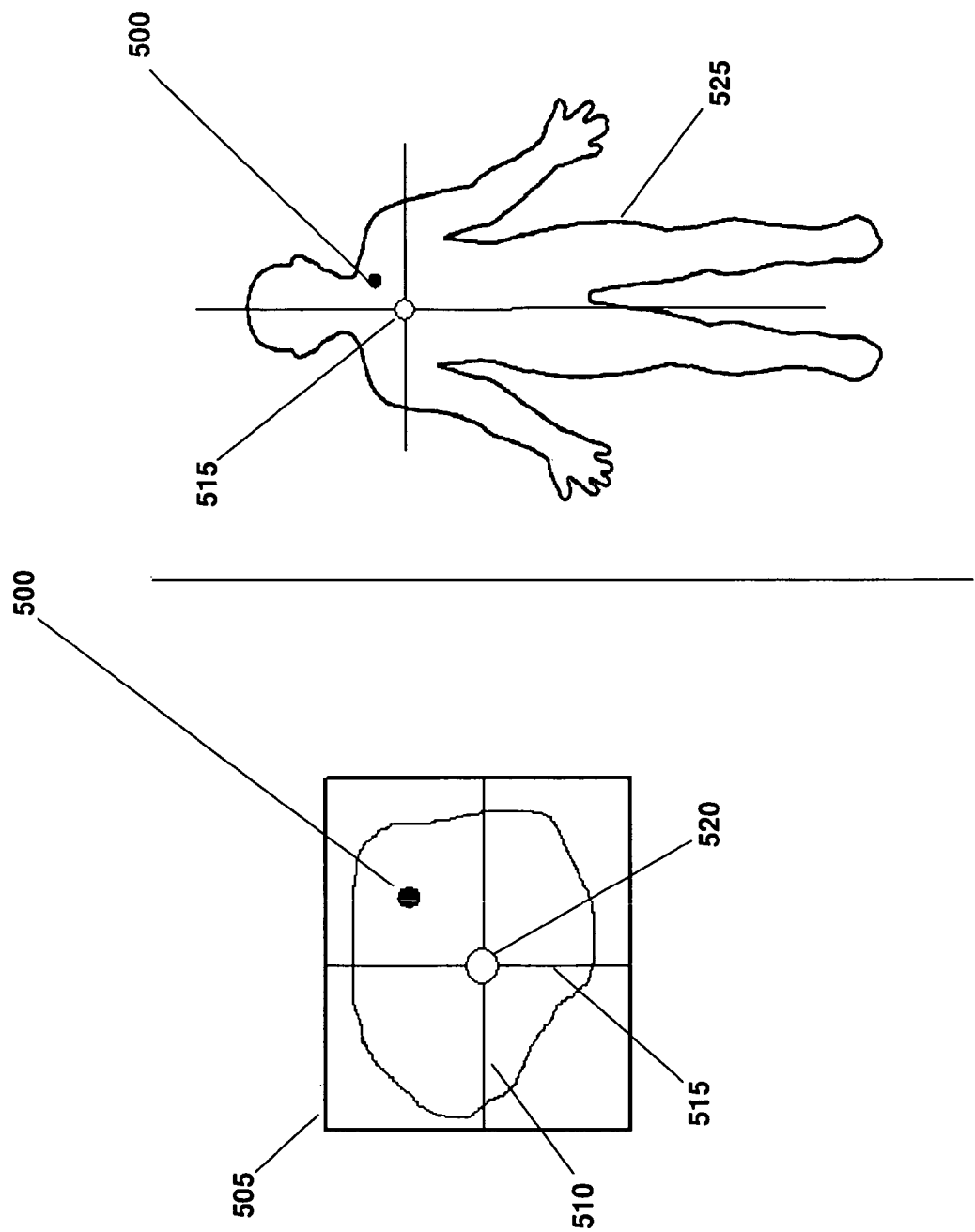
FIG. 5 illustrates the a guidance procedure used to calibrate the delivery of radiotherapy to a patient in accordance with various embodiments of the invention.

In other embodiments related to treatment fractions, it is more practical to first calculate the amount of movement required for alignment. This can be done, for example, by comparing the location of the contoured target area at time of treatment to the location of the same area at time of planning in order to calculate a virtual target shift. The position can also be calculated from the beam aperture information. The beam entry point at the required SSD should also be taken into account, however. This may be done, for example, by guiding the user to digitize the beam entry point corresponding to the virtual target shift on the patient's skin. As shown in FIG. 5, this guidance procedure can involve displaying the real-time position of the wand tip 500 in a beam's-eye view 505 relative to the central axis (i.e., the intersection of x and y axes 510, 515). The user then moves the pointer tip such that its position 500 corresponds to the central axis within a set tolerance 520. In order to help orient the user, it is useful to show a schematic model of the patient orientation on the display screen 525. The patient shift identified on the screen 525 that consider both cavity position and beam entry point, may then converted into physical couch shifts required to align the patient to the beam, and the shifts are actually carried out (either automatically, manually, or in some cases a combination of both) with the patient on the couch.

Figure 6:
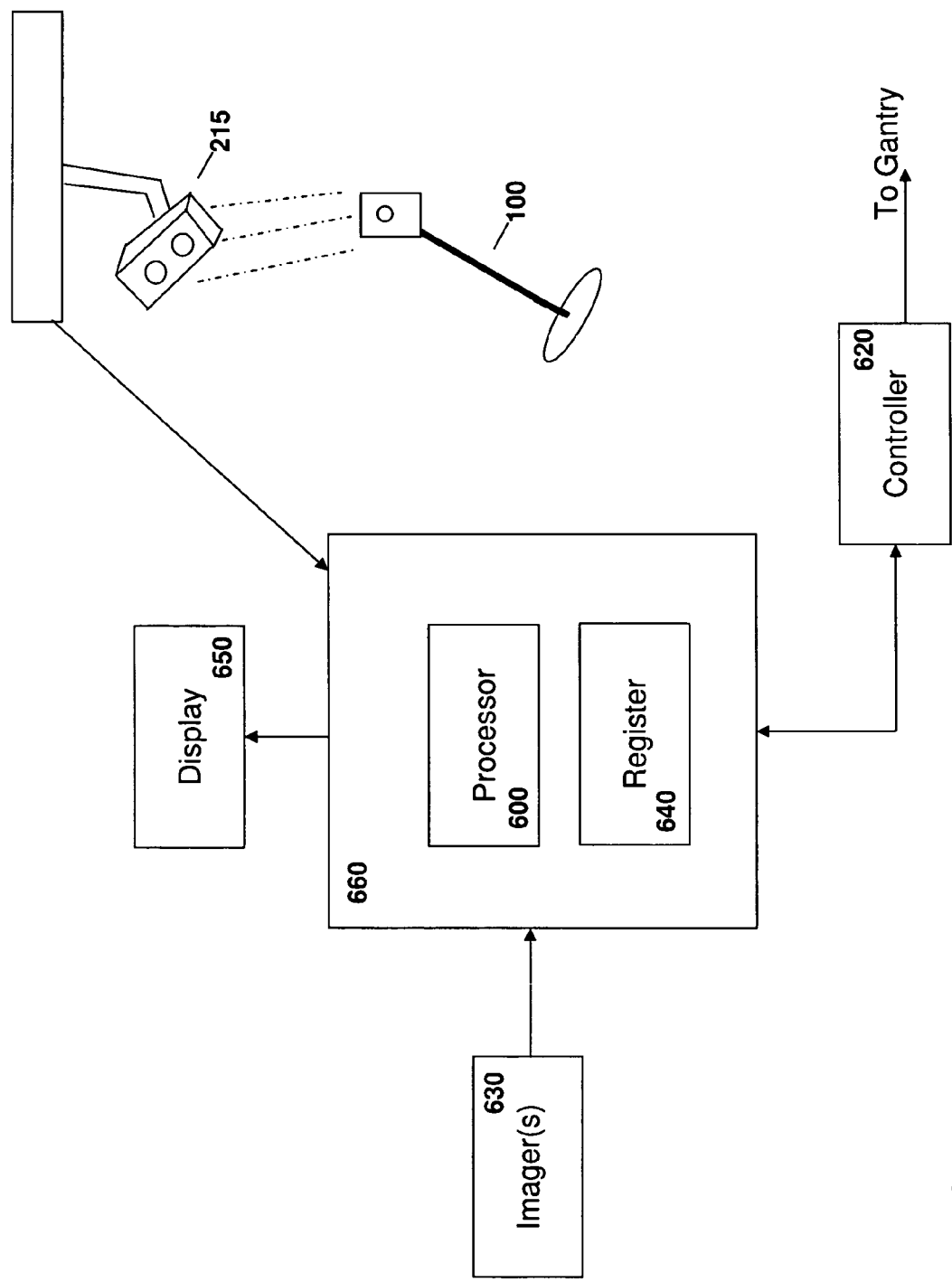
FIG. 6 schematically depicts a system for orienting a patient in preparation for delivery of radiotherapy treatment in accordance with various embodiments of the invention.

Referring to FIG. 6, a system for establishing radiation beam parameters for treatment of a patient includes the wand tool 100 and the tracking device 215 describe above, and a processor 600. The processor performs the calculations necessary to characterize the preferred beam trajectory and beam entry point based on tracking data received from the tracking device 215 as it follows the tool 100 about the patient. The processor may implement and execute the functionality described above using stored computer programming instructions, hardware components, or a combination of both. In some implementations, the parameters generated by the processor are provided to a controller 620, which causes a gantry and/or a gantry couch to move, thus properly aligning the beam and the patient according to the preferred beam angle, entry point and SSD.

As described above, image data related to the location and orientation of the tool 100 may be augmented with imaging data representative of internal and/or external anatomical features of the patient. In such cases, one or more imagers 630 may be used (e.g., MRI, CT, X-Ray, digital photography, etc.) to capture the images. The image data may then the transferred to and/or stored on a register 640 for subsequent use and display on one or more display devices 650.

In some embodiments, the processor 600 and register 630 may implement the functionality of the present invention in hardware or software, or a combination of both on a general-purpose or special-purpose computer 600. In addition, such a program may set aside portions of a computer's random access memory to provide control logic that affects one or more of the tool tracking, image manipulation, image fusion, display, and gantry control. In such an embodiment, the program may be written in any one of a number of high-level languages, such as FORTRAN, PASCAL, C, C++, C#, Java, Tcl, or BASIC. Further, the program can be written in a script, macro, or functionality embedded in commercially available software, such as EXCEL or VISUAL BASIC. Additionally, the software could be implemented in an assembly language directed to a microprocessor resident on a computer. For example, the software can be implemented in Intel 80×86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method for establishing radiation beam parameters for delivery of radiotherapy treatment to a patient using a radiotherapy treatment device, the method comprising:
  a. orienting a wand with respect to the patient to establish a beam entry point;
  b. acquiring positional parameters characterizing wand positioning with respect to a room coordinate system;
  c. defining, in the room coordinate system, a beam angle consistent with the beam entry point;
  d. obtaining one or more images of the patient's internal anatomy; and e. visually representing portions of the patient's internal anatomy within a beam area corresponding to the defined beam angle, wherein the visual representations of the patient's internal anatomy comprises digitized images of one or more internal anatomical features of the patient's anatomy according to a beam's eye view of a radiation treatment device, wherein the beam's eye view is oriented along the defined beam angle.

2. The method of claim 1 wherein wand positioning comprises a position of a tip of the wand.

3. The method of claim 1 wherein wand positioning comprises an orientation of the wand.

4. The method of claim 1 wherein orienting the wand further establishes a beam trajectory.

5. The method of claim 1 wherein orienting the wand further establishes a collimator rotation.

6. The method of claim 1 further comprising the step of converting the beam angle to couch and gantry movement parameters.

7. The method of claim 6 further comprising moving a gantry couch in accordance with the parameters.

8. The method of claim 7 wherein movement of the couch is tracked and feedback specifying conformance to the parameters is provided to a user.

9. The method of claim 1 wherein the beam angle is established relative to a curvature of the patient.

10. The method of claim 1 further comprising:
d. obtaining one or more images of the patient's external anatomy; and
e. visually representing portions of the patient's external anatomy within a beam area corresponding to the defined beam angle.

11. The method of claim 1 wherein the visual representation comprises image points on a plane defined relative to the beam angle.

12. The method of claim 11 where the plane is defined by a beam's-eye view.

13. The method of claim 11 where the plane is perpendicular to a beam's-eye view.

14. The method of claim 1 further comprising visually displaying beam information, the beam information comprising at least one of beam aperture, dose information, or electron beam depth.

15. The method of claim 1 further comprising establishing a beam entry point and correlating the beam entry point with a desired source-to-skin distance.

16. The method of claim 1 wherein the wand orientation defines a current source-to-skin distance, and further comprising defining a desired source-to-skin distance and computing couch and gantry movement parameters for shifting the current source-to-skin distance to the desired source-to-skin distance.

17. The method of claim 1 where the beam angle is used for treatment planning purposes.

18. A system for establishing radiation beam parameters for treatment of a patient, the system comprising:
a. a tool;
b. a tool tracking device for sensing an orientation of the tool with respect to the patient to establish at least a beam entry point;
c. a register for storing one or more images of the patient's internal anatomy; and
d. a processor for characterizing the beam entry point with respect to a room coordinate system, defining a beam angle consistent with the beam entry point and creating a visual representation of portions of the patient's internal anatomy within a beam area corresponding to the defined beam angle, wherein the visual representations of the patient's internal anatomy comprise digitized images of one or more internal anatomical features of the patient's anatomy according to a beam's eye view of a radiation treatment device, wherein the beam's eye view is oriented along the desired beam angle.

19. The system of claim 18 wherein the processor further characterizes a beam trajectory.

20. The system of claim 18 wherein the tool comprises a wand having a shaft, a handle, and a distal tip.

21. The system of claim 20 wherein the tool further comprises one or more optical tracking sensors identified by the tool tracking device.

22. The system of claim 18 further comprising a register for storing image data corresponding to one or more of the internal anatomical features of the patient and external anatomical features of the patient.

23. The system of claim 22 further comprising one or more imaging devices for obtaining the image data.

24. The system of claim 23 further comprising a display device for displaying the one or more of the internal and external anatomical features of the patient within a beam's eye view of a radiation treatment device.

25. The system of claim 24 wherein the display further provides beam information, the beam information comprising at least one of a beam aperture, a dose information, and an electron beam depth.

26. The system of claim 18 further comprising a controller for determining couch and gantry movement parameters, and directing movement of at least one of the gantry and the couch such that a radiation beam may be delivered to the patient along the desired beam angle.

27. The system of claim 26 wherein the processor correlates the beam entry point with a desired source-to-skin distance.

28. The system of claim 27 wherein the tool orientation defines a current source-to-skin distance, the controller computing couch and gantry movement parameters for shifting the current source-to-skin distance to the desired source-to-skin distance.

* * * * *